United States Patent
Glynn, Jr. et al.

(10) Patent No.: US 8,846,016 B2
(45) Date of Patent: Sep. 30, 2014

(54) HAIR TREATMENT COMPOSITIONS

(75) Inventors: John R. Glynn, Jr., Ridgewood, NJ (US); Ajay G. Dingley, New Windsor, NY (US); Mark S. Garrison, Suffern, NY (US); Shari Martin, Suffern, NY (US)

(73) Assignee: Avon Products, Inc., New York, NY (US)

( * ) Notice: Subject to any disclaimer, the term of this patent is extended or adjusted under 35 U.S.C. 154(b) by 1260 days.

(21) Appl. No.: 12/097,932

(22) Filed: Jun. 18, 2008

(65) Prior Publication Data

US 2010/0021410 A1    Jan. 28, 2010

Related U.S. Application Data

(63) Continuation-in-part of application No. PCT/US2006/045792, filed on Nov. 30, 2006, which is a continuation-in-part of application No. 11/314,889, filed on Dec. 21, 2005.

(51) Int. Cl.
| | |
|---|---|
| *A61Q 5/12* | (2006.01) |
| *A61K 8/34* | (2006.01) |
| *A61K 8/41* | (2006.01) |
| *A61K 8/81* | (2006.01) |
| *A61K 8/58* | (2006.01) |
| *A61K 8/894* | (2006.01) |
| *A61Q 5/00* | (2006.01) |
| *A61K 8/70* | (2006.01) |
| *A61Q 5/06* | (2006.01) |
| *A61K 8/897* | (2006.01) |
| *A61K 8/73* | (2006.01) |

(52) U.S. Cl.
CPC . *A61K 8/585* (2013.01); *A61K 8/34* (2013.01); *A61K 8/416* (2013.01); *A61K 8/8176* (2013.01); *A61K 8/894* (2013.01); *A61Q 5/00* (2013.01); *A61Q 5/12* (2013.01); *A61K 8/70* (2013.01); *A61Q 5/06* (2013.01); *A61K 8/897* (2013.01); *A61K 8/737* (2013.01)
USPC .................. 424/70.12; 424/70.11; 424/70.21; 424/70.22; 424/70.27; 424/70.31

(58) Field of Classification Search
CPC ..... A61K 8/897; A61K 8/416; A61K 8/8176; A61K 8/585; A61K 8/737; A61K 8/894; A61K 8/70; A61K 8/34; A61Q 5/12; A61Q 5/00; A61Q 5/06
See application file for complete search history.

(56) References Cited

U.S. PATENT DOCUMENTS

| | | | |
|---|---|---|---|
| 3,814,110 A * | 6/1974 | Cassidy ...................... 132/202 |
| 4,135,524 A | 1/1979 | Rosenberg et al. |
| 4,183,367 A | 1/1980 | Goebel et al. |
| 5,124,467 A | 6/1992 | Rodger et al. |
| 5,567,428 A * | 10/1996 | Hughes ........................ 424/401 |
| 5,914,310 A | 6/1999 | Li et al. |
| 6,156,298 A | 12/2000 | Karlen et al. |
| 6,203,780 B1 | 3/2001 | Arnaud et al. |
| 6,503,413 B2 | 1/2003 | Uchiyama et al. |
| 7,504,093 B2 | 3/2009 | Bracken et al. |

FOREIGN PATENT DOCUMENTS

EP    2003/426986 A2    7/2003

OTHER PUBLICATIONS

Silicone Polyether Surfactants and Derivatives, SPSD, Technical Data Sheet, Siltech, 2004.*
O'Lenick, Anthony J. Jr.; Silicone Emulsions and Surfactants, Journal of Surfactants and Detergents, vol. 3, No. 3 (Jul. 2000), p. 387-393.
International Cosmetic Ingredient Dictionary and Handbook, Tenth Edition, 2004, vol. 2, p.
Silicone Polyether Surfactants and Derivatives. Technical data sheet [online]. Siltech, LLC, Jun. 1, 2004.
Dupont Zonyl & Forafac fluroadditives. General brochure [online]. Dupont, Inc. 2001.
Global New Products Database, Record ID 207230, L'Oreal Fast Dry Shampoo, May 2003.
Global New Products Database, Record ID 10160288, Paul Mitchell Super Skinny Serum, Jan. 2004.
Global New Products Database, Record ID 209057, Sara Lee Next Generation Strong Gel, Jun. 2003.
Noveon Ultrasil, Beyond Conditioning Fast Drying Hair Care Porduts with Ultrasil Silicones, Apr. 2004.
Noveon Ultrasil, Ultrasil Q-Plus Quaternary Silicone, Jul. 2003.
Clearco Products Co., Inc., Cyclo-2244 (D4) Cyclomethicone Fluid Product Information, Aug. 20, 2012.

* cited by examiner

*Primary Examiner* — Lezah Roberts
*Assistant Examiner* — Nannette Holloman
(74) *Attorney, Agent, or Firm* — David M. Loyal; Joan M. McGillycuddy

(57) ABSTRACT

An aqueous and/or aqueous alcoholic leave-in composition to reduce the time to dry wet hair containing (a) at least one wetting agent having a Draves wetting value of 100 seconds of less selected in an amount sufficient to enhance the hydrophobicity of hair thereby causing water to dewet the hair, and optionally (b) at least one volatile selected from the group consisting of alcohols, dimethicone, trimethicone, and cyclomethicone and a method of shortening the time to dry wet hair.

23 Claims, No Drawings

HAIR TREATMENT COMPOSITIONS

CROSS-REFERENCE TO PRIOR APPLICATION

This continuation-in-part application claims the benefit of PCT Application Serial No. PCT/2006/45792 filed Nov. 30, 2006, which in turn claims priority to U.S. application Ser. No. 11/314,889 filed Dec. 21, 2005.

FIELD OF THE INVENTION

The present invention concerns a method for improving the drying time of hair that is wet, for example, after bathing, shampooing, swimming, and the like. In a preferred embodiment the invention concerns hair styling compositions that are applied to wet hair as a leave-in treatment for hair that additionally reduces the time to dry the hair during styling.

STATE OF THE ART

A common complaint of women, particularly those with long hair, is that it takes too long to dry and style their hair. Additionally, hair is often damaged by prolonged exposure to heat from a hair blower. One proposed solution to these problems is described in U.S. Pat. No. 5,567,428 in which compositions are disclosed comprising (a) a polysiloxane-grafted adhesive polymer, (b) a volatile, water insoluble solvent for the said polymer, and (c) a non-volatile, drying aid for the polymer that is soluble in the solvent, which composition forms a film on the hair.

Paul Mitchell's Super Skinny claims reduction of hair drying time by penetrating deep into the hair shaft, which displaces water and constricts the hair to a tighter diameter, thereby helping to reduce drying time. A tighter diameter is said to increase the surface area per volume, thereby increasing the rate of water evaporation to reduce drying time.

OBJECTS OF THE INVENTION

It is an object of the present invention to provide a method to improve the drying of hair following showering, bathing, swimming, shampooing, or the like, by changing the hydrophobicity of the hair shaft to cause dewetting of the hair.

It is a further object of the present invention to provide novel hair treatment compositions that reduce the time for drying, the compositions containing wetting agents to cause dewetting and sheeting of water off hair without binding the wetting agent to hair.

A further object is to provide hair treatment compositions that reduce the time to dry wet hair and that also style the hair.

Still another object of the invention is to provide hair treatment compositions that reduce the time to dry wet hair and that also condition the hair.

Yet another object of the invention is to provide a method of reducing damage to hair by reducing the time to dry the hair.

A further object is to improve the flexibility and manageability of hair by maintaining hair in a partly hydrated condition.

These and other objects and advantages of the invention will become obvious from the following detailed description.

SUMMARY OF THE INVENTION

The compositions of the invention are aqueous or hydroalcoholic hair treatment compositions comprising at least one wetting agent. When applied to wet hair, the presence of the wetting agent imparts hydrophobicity to the hair. As a consequence, water present on the hair tends to bead up and is more easily removed, for example by gravity, by toweling, by brushing, or by combing. Applicants have further found that the time to dry the hair is reduced, whether by air drying, towel drying, or blow drying. Suitable wetting agents may be selected from the group consisting of silicone polyether surfactants, fluorinated polymers, fluorinated surface active agents, Gemini surfactants, and combinations thereof.

In another aspect of the invention, the compositions of the present invention are hair styling compositions that are applied to damp hair, e.g., hair that has been partially dried by air drying, towel drying, or blow drying. Damp hair to which the styling compositions containing the at least one wetting agent are applied is more easily dried, and styling is found to be easy and quick.

In another embodiment the compositions of the present invention are aqueous or hydroalcoholic hair treatment compositions comprising (a) at least one wetting agent; (b) at least one hair treatment component; (c) water, and optionally (d) at least one volatile solvent.

The hair treatment compositions may contain from about 10 to 99% by weight water; 0.05 to 10% by weight wetting agent; 0.01 to 10% by weight of hair treatment component selected from the group consisting of hair fixative agents, hair conditioning agents, and mixtures thereof, and 0 to 55% by weight of the volatile solvent. The hair treatment compositions may be in the form of a gel, mousse as either an aerosol or pump, cream, spray as either an aerosol or pump, putty, spray wax, pomade, brilliantine, lotion, balm, stick, strip, solution, dispersion, or emulsion. The products are leave-in products that are applied to wet hair, any may be used to treat the hair, for example, styling products and fixative products; products to provide a gloss to hair, or products to condition hair to make it more manageable.

DETAILED DESCRIPTION OF THE INVENTION

The compositions of the present invention are intended for application to wet hair, in particular human hair on the head of the user, as leave-in products. Wet hair includes hair, such as damp hair, e.g., hair that has been dried to remove some or all of the surface water on the hair shaft, but remains substantially hydrated, i.e., where water has permeated the hair shaft and is residual within the hair shaft. The compositions are formulated so that the time needed to subsequently dry the hair is reduced. To this end the compositions contain a wetting agent. When applied to wet hair, the wetting agent lowers the surface tension of the hair and imparts substantial hydrophobicity to the hair. This enhanced hydrophobicity causes the water present on the hair to bead on the hair, and also permits the water droplets to run from the hair due to gravity or other forces, such as combing, brushing, or the force of air from a blow dryer. This process is referred to as sheeting. By removing excess water, hair that has been treated with the wetting agent will be dried more easily, i.e., in less time, whether air dried, towel dried, or blow dryer dried. In particular the compositions and methods of the present invention are especially suitable for hair longer than about three inches and especially longer than about six inches.

While not wishing to be bound by any theory or mechanism of action, it is also believed that the wetting agent, especially in concert with a hair styling agent, provides a film on the hair that causes some of the water that has penetrated the hair cuticle to remain within the hair shaft. This additionally reduces the amount of water that is to be removed from the hair, thereby reducing drying time. Moreover, residual water in the hair (i.e., hydrated hair) would impart greater flexibility and manageability to the hair, and reduce split ends. Reduction in the time to dry hair by blow drying also results in less damage to the hair.

In one aspect of the invention there is provided a method for reducing the time to dry wet hair, for example, drying wet hair following showering, shampooing, bathing, swimming, and the like, comprising applying to wet hair an aqueous or hydroalcoholic composition containing the wetting agent, and subsequently drying the hair. Before or during the drying step, the hair may be mechanically processed to help water to sheet from the hair. Such processing includes brushing, combing, toweling, and the like. In the case of toweling, it is seen that mechanical action is typically combined with absorbing of the water present on the hair. In the case of blow drying of the hair, it is seen that the force of the hot air from the dryer will also cause the water to sheet from the hair. In this embodiment, the composition comprises the wetting agent in an aqueous or hydroalcoholic vehicle. Surprisingly, the time to dry the hair is reduced, notwithstanding the application to hair of additional water.

In another aspect of the present invention there is provide a composition and method for styling the hair while simultaneously reducing the time to dry the hair. As previously recited, the method for reducing the time to dry wet hair, for example, drying wet hair following showering, shampooing, bathing, swimming, and the like, comprises applying to wet hair an aqueous or hydroalcoholic hair styling composition comprising the wetting agent, a styling component, water and optionally a volatile solvent, and subsequently drying the hair. Before or during the drying step, the hair may be mechanically processed to help water to sheet from the hair. Such processing includes brushing, combing, toweling, and the like. In the case of toweling, it is seen that mechanical action is typically combined with absorbing of the water present on the hair. In this embodiment, the composition comprises the wetting agent in an aqueous or hydroalcoholic vehicle. Surprisingly, the time to dry the hair is reduced, notwithstanding the application to hair of additional water present in the composition.

In another aspect of the invention, the compositions of the present invention are hair styling compositions that are applied to damp hair, e.g., hair that has been partially dried by air drying, towel drying, or blow drying. Damp hair to which the styling compositions containing the at least one wetting agent are applied is more easily dried, and styling is found to be easy and quick. Such compositions are characterized by containing, in addition to the wetting agent, one or more hair treatment agents adapted to help style the hair.

All concentrations in the specification and claims are percent by weight of the total composition on an active ingredient basis, unless indicated to the contrary.

The Wetting Agent

Wetting agents for use in the compositions of the present invention are characterized by an ability to lower the surface tension of the hair. Thus, the wetting agents typically have a surface tension in the range of from about 15 to about 26, and preferably from about 17 to about 23 dynes/cm (mN/m). The surface tension of the wetting agents is the equilibrium surface tension at 25° C., which is independent of concentrations above the critical micelle formation concentration (CMC). Equilibrium surface tension is measured, for example by Wilhemy plate, DuNouy ring or pendant drop shape analysis methods. See www.kruss.info/techniques/surface_tension_e.html.

The wetting agents useful in the compositions of the present invention are further characterized as having a Draves wetting value of less than 100 seconds, preferably less than 30 seconds, and most preferably less than 20 seconds. The Draves wetting value is determined in accordance with ASTM D2281-68. In this test 0.5 g wetting agent is added to one liter of tap water in a 1000 ml beaker and thoroughly mixed. A 45 cm (5 g) Drave 40/2 cotton skein folded in two to a length of about 22 cm is bound with thread to a wire loop having a 40 g lead weight attached thereto with a copper "s" hook. The other end of the skein is cut with scissors to leave it open. The lead weight is then gently placed at the water's surface and dropped into the beaker while measuring the time it takes for thread between the lead weight and the wire hook to slacken. The process is repeated with two other skeins and the average of the three tests is taken.

Additionally, in some cases the wetting agents are superwetting agents. Superwetting is defined by the ability of a 1% aqueous solution of the wetting agent to spread on a paraffin substrate without mechanical means. A time of less than 10 seconds, preferably less than 8 seconds, denotes superwetting for the wetting agent. See Randal M. Hill, Surfactant Science Series, v. 86 (Marcell Dekker 1999).

When present in an effective amount, a film of the wetting agent is formed on the hair, and allows water to bead on the hair, and to drain from the hair by gravity. It has been found that the compositions of the present invention containing the wetting agent and in particular the superwetting agent, reduce drying time of hair by blow drying by 15% or more, preferably by 25% or more, and most preferably 50% or more.

The wetting agent is generally present in the composition in an amount of from about 0.05 to 10 wt. %, preferably from about 0.1 to 5 wt. %, and most preferably from about 0.5 to 2 wt. %. The amount of wetting agent tends to be proximate the low end of the range when it is a superwetting agent.

The preferred wetting agents are selected from the group consisting of silicone polyether surfactants, fluorinated polymers and surface active agents, gemini surfactants, fluorosilicones, and combinations thereof.

Silicone polyether surfactants are silicone polymers that have a polysiloxane backbone and onto which is provided an ethoxylated and/or propoxylated chain to impart surface activity. Suitable silicone polymers have the structural formula:

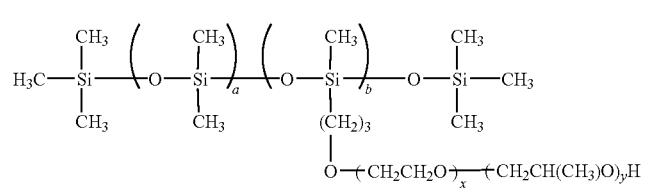

I wherein a is an integer of from 0 to 6; preferably 1 to 3; b is an integer of from 1 to 12, preferably 2 to 4; x is an integer of from about 6 to about 12, preferably about 8, and y is an integer of from about 0 to about 3, preferably 0. The silicone polyether surfactants typically have a molecular weight of less than about 10,000, preferably less than about 5,000, and most preferably from about 600 to about 2,500. Preferred is the family of silicone polyethoxylated polymers sold under the tradename Silsurf sold by Siltech LLC (Dacula, Ga.), for example Silsurfs A-008, A-208, B-208 and C-208. Also suitable is Q2-5211 Superwetting Agent sold by Dow Corning.

Suitable wetting agents also include fluorinated polymers and fluorinated surface active agents.

Fluorinated polymers include polyperfluoroethers, for example, polyperfluoromethylisopropyl ether sold as Fomblin HC/01 and HC/02 by Solvay, and polyperfluoroethoxymethoxy difluoromethyl ether sold as Fomblin HC/H-50 and HC/H-100, also by Solvay.

Suitable ethoxylated fluorosurfactants have chemical structure

$$R_f CH_2 CH_2 O(CH_2 CH_2 O)_x H \qquad \text{II}$$

Wherein $R_f$ is $F(CF_2 CF_2)_n$; n is an integer of 3 to 8, and x is an integer of from 0 to 30. These compounds are sold by Dupont under the name Zonyl, for example, Zonyl FSN, FSN-100, FSO-100, and FS-300. Also suitable is Zonyl FS-310.

Another class of fluorosurfactants materials are anionic fluorosurfactants, for example, DEA C8-16 perfluoroalkylethyl phosphate sold as Zonyl RP and ammonium $C_6$-$C_{16}$ perfluoroalkylethyl phosphate sold as Zonyl FSP, both by Dupont. Also suitable are fluorinated cationic, amphoteric, and zwitterionic fluorosurfactants, for example, polytetrafluoroethylene acetoxybetaine (Zonyl FSK) and $C_4$-$C_{18}$ perfluoroalkylethyl thiohydroxypropyltrimonium chloride (Zonyl FSD).

Also suitable is perfluorodecalin, also known as decalin perfluoride, is a fully fluorinated, odorless liquid whose surface tension is 17.6 mN/m sold under the tradename Flutec PC 6 by F2 Chemicals.

Another suitable fluorinated surfactant is perfluorocyclohexyl methanol, a fully fluorinated 1-hydroxymethyl cyclohexane compound, which is available from C.I.T. sold as Fiflow PB145.

Also suitable are fluorosilicones, such as perfluorononyl dimethicone, a fluorinated silicone containing 14% fluorine, which is sold by Biosil Technologies, Inc. under the tradename Biosil Basics Fluorosil 14. It is soluble in cyclomethicone and silicone fluid 350 vis, but insoluble in water, propylene glycol, and mineral oil. Another fluorosilicone material is perfluorononylethyl carboxydecyl lauryl dimethicone sold as Pecosil FST-412 by Phoenix.

The wetting agents may be gemini surfactants. These are also known as dimeric surfactants, and consist of two conventional surfactant molecules each having a terminal hydrocarbon tail and polar head groups that may be cationic, anionic or nonionic and chemically bonded together by a spacer that maybe long or short, flexible or rigid. See B. S. Sekhon, Gemini (Dimeric) Surfactants, The Two-Faced Molecules, Resonance, p. 42 (March 2004). Suitable Gemini surfactants are 2,5,8,11-tetramethyl-6-dodecyn-5,8-diol sold as Dynol 604 by Air Products and 2,4,7,9-tetramethyl-5-dodecyn-4,7-diol sold as Surfynol 104, -700 and -2502 or under the tradename Envirogem, all by Air Products.

The Hair Treatment Agent

The hair treatment compositions of the present invention preferably comprise at least one hair treatment agent. The hair treatment agents for use in the hair treatment compositions of the present invention are especially hair fixative agents, hair conditioner agents, and mixtures thereof. The hair treatment agents permit the consumer to style the hair in conjunction with combing or brushing, and especially coincidental to drying with a blow dryer or other device that supplies heat to the hair. The hair treatment compositions are especially applied to damp hair.

The hair fixative agents are typically polymers that provide a more rigid film on the hair following application and keep the hair in place after styling, i.e., by combing or brushing. The hair fixatives work by keeping a plurality of hair strands stuck together by adhesive forces. Thus, the fixative polymers are usually thought of as resins or gums.

The hair fixative agents are often cationic polymers, but may also be nonionic, anionic, and amphoteric polymers. Suitable hair fixative agents are identified in the International Cosmetic Ingredient Dictionary and Handbook, v. 3, p. 2227-8 ($10^{th}$ Edition 2004) published by the Cosmetics, Toiletries and Fragrance Association (CTFA) (hereinafter referred to as "INCI").

The hair conditioning agents are typically cationic polymers that provide softness to the hair or that repair damaged hair. The conditioning polymers generally provide a film on the hair that is smooth and not tacky. Typically, the conditioning polymers are cationic but may also be nonionic, zwitterionic, and amphoteric. The hair conditioning agents may also be oils, as described in greater detail below.

As known in the art, there is some overlap between polymers that provide hair conditioning benefit and hair fixative benefits, depending often on the concentration of the polymer and the other components present in the formulation.

Among the suitable nonionic polymers, mention may be made of homo- and copolymers of vinylpyrrolidone, especially, copolymers of vinylacetate, in particular those sold under the trade name Luviskol, e.g., homopolymers Luviskol K 30, K 60 or K 90; copolymers Luviskol VA 55, VA 64; and the terpolymer vinylpyrrolidone/vinylacetate/vinylpropionate copolymer sold as Luviskol V AP 343 all from BASF; vinyl pyrrolidone/acrylates copolymer; vinyl pyrrolidone/hexadecane copolymer, and vinyl pyrrolidone/vinyl caprolactam/dimethylaminoethyl methacrylate acrylates copolymer. Other nonionic polymers suitable as the hair fixative agent include VP/acrylates/lauryl methacrylate copolymer; adipic acid/diethylenetriamine copolymer; PEG-8/SMDI copolymer; polyacrylamide-1; polyvinyl acetate; PPG-12/SMDI copolymer; polyurethane-1, polyurethane-14; and polyimide-1 sold as Aquaflex XL-30 by ISP.

Natural nonionic hair fixative polymers and derivatives suitable for the composition of the present invention neutralized shellac and its derivatives; guar gum; rhizobian gum; rosin acrylate, xanthan gum and dehydroxyxantham gum; cellulose derivatives, including hydroxypropyl cellulose and hydroxylethylcellulose; and yeast palmitate. Also suitable are inorganics such as magnesium aluminum silicate (Veegum) to thicken hair.

Suitable cationic hair-fixative polymers are those having the INCI category name Polyquaternium. Typical examples are Polyquaternium-4, Polyquaternium-6, Polyquaternium-7, Polyquaternium-10, Polyquaternium-11, Polyquaternium-16, Polyquaternium-22 and Polyquaternium-28, Polyquaternium-37, Polyquaternium-55, and Polyquaternium-68 with Polyquaternium-11 (sold as Gafquat from ISP and as Luviquat PQ from BASF) and Polyquaternium-37 (Salcare SC-95) preferred.

Amphoteric or zwitterionic polymers, preferably used in mixture with at least one nonionic and/or cationic polymers, are also found to be suitable for styling compositions of the present invention. Examples are copolymerisates of N-octylacrylamide, acrylic or methacrylic acid and tertbutylaminoethylmethacrylate known with its trade name Amphomer; copolymers of methacryloylethylbetaine and alkyl methacrylate known as Yukaformer; terpolymer of methacrylic or acrylic acid, itaconoic acid and a basic monomer of mono- or dialkylaminoalkyl acrylate or a methacrylate or acrylate of methacrylamide, known with the trade name Aquaflex SF 40.

Anionic polymers are as well suitable for styling compositions of the present invention. Suitable ones are vinyl alkyl ethers, in particular methyl vinyl ether/maleic acid copolymers, distributed under the trade name Gantrez AN or ES. These polymers may also be partly esterified, as for example, Gantrez ES 225 or ES 435. Further useful anionic polymers are acrylates copolymer, acrylates/vinyl acetate copolymer; vinyl acetate/crotonic acid or vinyl acetate/vinyl neodecanoate/crotonic acid copolymers of the type Resyn; sodium acrylate/vinyl alcohol copolymers; sodium polyacrylate, sold as A100 by ISP; sodium polystyrene sulfonate, e.g., Flexan 130; ethyl acrylate/acrylic acid/N-tert-butyl acrylamide copolymers of the type Ultrahold; vinyl pyrrolidone/vinyl acetate/itaconic acid co-polymers; and acrylic acid/acrylamide copolymers or the sodium salts thereof of the type Reten.

The hair fixatives are typically present in an amount of from about 0.01 to about 10%, preferably 0.1 to 5%, and preferably 1 to 5%, by weight of the total composition.

The treatment composition of present invention can comprise hair conditioning agents. Conditioning agents can be selected from oily substances, nonionic substances, amphoteric ingredients, and cationic substances or their mixtures.

Oily substances are selected from among nonvolatile silicone oils, natural oils, and synthetic oils.

Among silicone oils suitable as a conditioning agent are dimethicone, dimethiconol, polydimethylsiloxane, DC Fluids from Dow Corning; polysilicones, such as polysilicone-1, polysilicone-2, polysilicone-5, polysilicone-10, polysilicone-14; dimethiconol/IPDI copolymer; and bis-PPG-15 dimethicone/IPDI copolymer.

Natural oils suitable herein are olive oil, almond oil, avocado oil, squalane, mineral oil, and combinations thereof. Suitable synthetic oils include the hydrogenated organic compounds, such as hydrogenated polydecene, hydrogenated rice bran oil, hydrogenated myristyl olive esters, and the like. Other nonionic conditioning agents are polyols such as glycerin, glycols, such as phytantriol, and low molecular weight polyethylene glycols known with trade names Carbowax from Union Carbide and Polyox WSR from Amerchol, polyglycerins, and polyethylene glycol mono- or di-fatty acid esters having general Formula III and IV, respectively,

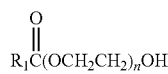

III

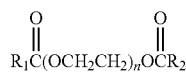

IV wherein $R_1$ and $R_2$ are independent from each other, and may be a saturated or unsaturated, branched or nonbranched alkyl with 7 to 21 carbon atoms and n is typically 2 to 100.

The hair treatment compositions can contain further cationic conditioning ingredients according to the Formula V.

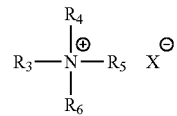

V wherein $R_3$ (i) is a saturated or unsaturated, branched or nonbranched alkyl with 8 to 22 carbon atoms; (ii) has the structure $R_7CONH(CH_2)_n$ wherein $R_7$ is a saturated or unsaturated, branched or nonbranched alkyl with 7 to 21 carbon atoms and n has typical value of 1-4; or (iii) has the structure $R_8COO(CH_2)_n$ wherein $R_8$ is a saturated or unsaturated, branched or nonbranched alkyl with 7 to 21 carbon atoms and n has typical value of 1-4;

wherein $R_4$ (i) is H or a unsaturated or saturated, branched or nonbranched alkyl with 1 to 22 carbon atoms; (ii) has the structure $R_7CONH(CH_2)_n$, or (iii) has the structure $R_8COO(CH_2)_n$, wherein $R_7$, $R_8$ and n are same as above;

wherein $R_5$ and $R_6$ are individually hydrogen or an alkyl of an integer of 1 to 4 carbon atoms, and $X^-$ is an anion.

Typical examples of compounds of structure V are cetyl trimethyl ammonium chloride, steardimonium chloride, dipalmitoyl dimonium chloride, distearyl dimethyl ammonium chloride, stearamidopropyl trimonium chloride, dioleolethyl dimethyl ammonium methosulfate, and diolcoylethyl hydroxyethylmonium methosulfate. The quaternized hair conditioning agent compounds can also serve as solubilizing agents for those ingredients difficult to integrate into the formulations. Other cationic hair conditioning actives include quaternium-8; quaternium-14; quaternium-15; quaternium-18; quaternium-22; quaternium-24; quaternium-26; quaternium-27; quaternium-30; quaternium-33; quaternium-37; quaternium-53; quaternium-60; quaternium-61; quaternium-72; quaternium-78; quaternium-80; quaternium-81; quaternium-82; quaternium-83; quaternium-84; and quaternium-91.

Especially useful are the cationic cellulose polymers such as Polyquaternium-10 sold as UCARE Polymer JR from Amerchol and cationic guar gum known with trade name Jaguar from Rhone-Poulenc, for example guar hydroxypropyltrimonium chloride.

Suitable cationic polymers to condition hair also include quaternized silicones such as silicone quaternium-3, silicone quaternium-4, and silicone quaternium-8. Silicones with aminofunctional groups such as amodimethicone are also suitable.

The conditioning agents further include hydrolyzed organic materials such as hydrolyzed casein; hydrolyzed collagen; hydrolyzed hair keratin; hydrolyzed milk protein; hydrolyzed jojoba esters; hydrolyzed soy protein; hydroxypropyltrimonium hydrolyzed rice bran protein; palmityoyl hydrolyzed pea amino proteins; amino acids; peptides, and the like.

Useful amphoteric or zwitterionic surfactants are in particular the various known betaines such as fatty acid amido alkyl heroines and sulfobetaines, for example, lauryl hydroxy sulfobetaines, long-chain alkylamino acids such as cocoaminoacetate, cocoaminopropionate and sodium cocoamphopropionate and -acetate.

Also useful amphoteric and zwitterionic substances include betaines of the structure:

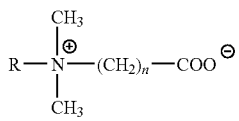

(VI)

wherein R is a $C_8$-$C_{18}$ alkyl group and n is 1 to 3, sulfobetaines of the structure:

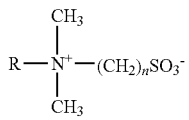

(VII)

wherein R is a $C_8$-$C_{18}$ alkyl group and n is 1 to 3, and amido alkylbetaines of the structure:

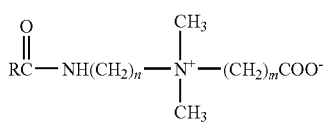

(VIII)

wherein R is a $C_7$-$C_{18}$ alkyl group and n and m is 1 to 3. Preferred are fatty acid amidoalkyl betaines, especially cocoamidopropyl betaine, and cocoamphoacetate and propionate, in particular the sodium salts thereof.

Typical concentration range for any of the conditioners mentioned above can be 0.01 to 10% by weight, preferably 0.1 to 5% by weight, and more preferably 1 to 5% by weight. Hair fixatives agents and hair conditioning agents can both be present in the compositions of the invention, typically in a combined amount of from about 0.1 to 10% by weight of the total composition.

Hair conditioning agents suitable herein are tabulated at INCI, v. 3, p. 2217-27. Of course, hair treatment agents that might be incompatible with any particular wetting agent should be avoided.

Solvent System

The compositions of the present invention are aqueous or hydroalcoholic. The compositions may contain from about 10 to 99% water by weight of the composition, preferably from 35 to 95% by weight. In the hydroalcoholic compositions, the low molecular weight alcohol component may comprise up to about 55% alcohol, typically from about 1 to 55% alcohol, and preferably 10 to 40% alcohol. Whether the composition is aqueous or hydroalcoholic depends on the choice of other ingredients in the composition, including the hair styling component and the need for an alcohol based solvent for solubilization. Suitable alcohol components are the low molecular weight $C_1$ to $C_8$ alcohols, especially ethanol, isopropanol, and butanol. Also useful are the low molecular weight $C_1$ to $C_8$ polyols, in particular propylene glycol, butylene glycol, and hexylene glycol.

The solvent system may further comprise other volatile organic and inorganic solvents that do not exhibit the interfacial properties of the wetting agent, such as cyclomethicone, low molecular weight dimethicone, trimethicone, and mixtures thereof. The term "volatile" means the oil has a measurable vapor pressure, or a vapor pressure of at least 2 mm of mercury at 20° C. The other solvent components may be present in the compositions in an amount of up to about 25%, preferably from 0.001 to 10%, and especially 0.01 to 5%, by total weight of the composition.

Optional Components

Additional functional components may be incorporated in the compositions, in amounts effective to provide their functional benefits, as is know in the art.

Among the functional ingredients, mention may be made of emollients, humectants, sunscreen agents and UV light absorbers, preservatives, fragrances, sequestrants, chelating agents, antioxidants, pH modifiers and dyes. Additionally, solubilizing agents suspending agents, and stabilizers may be incorporated to ensure that the actives are maintained in solution or in a stable emulsion. Thickeners may be incorporated to provide the proper consistency to the formulation. Propellants may be incorporated in aerosol and mousse products.

Suitable materials are set forth in INCI, v. 3, Section 4.

The present invention can comprise sunscreens and/or UV filters present either for stabilization of the product color or for protection of hair from environment influences such as loss of elasticity, loss of hair color (bleaching effect of sun light). Suitable substances are:

4-Aminobenzoic acid and its esters and salts, cinnamic acid and the esters and salts thereof, 4-methoxycinnamic acid and the esters and salts thereof, salicylic acid and the esters and salts, 2,4-dihydroxybenzophenone.

The compositions of the present invention may be made simply by mixing the required ingredients. In the case of hair styling compositions, the procedures generally used for like products not containing the wetting agent can be employed, with the wetting agent being incorporated in the aqueous phase by simple mixing.

In the following examples, there are described several preferred embodiments to illustrate the invention. However, it should be understood that the invention is not intended to be limited to the specific embodiments. The concentrations are on a weight basis of active ingredient, unless the activity is otherwise indicated, either in the description of the component or in a footnote.

Example 1

A hair conditioner composition in accordance with the present invention was prepared comprising 98.895% demineralized water; 1.0% PEG-8 dimethicone (2100 MW) available as Silsurf C-208 from Siltech. LLC, which is a 90% active silicone polyethylene ether surfactant having an average of 8 moles ethylene oxide in a poly(ethylene oxide/prolpylene oxide) monoalkylether diluent; 0.1% dimethicone copolyol, and 0.005% wheat amino acids.

Example 2

A hair conditioner in accordance with the present invention was prepared comprising 48.895% demineralized water, 50% alcohol SD40B, 1% Silsurf C-208, 0.1% dimethicone copolyol, and 0.005% wheat amino acids.

The compositions of Examples 1 and 2 were tested on 10 females each of various hair types in a standard, blinded half-head comparison wherein an expert evaluator shampooed the hair with a standard shampoo and rinsed. The hair was then parted in the middle and the test product was applied to one side and a control of water to the other. Two expert evaluators each dried one side of the head with identical dryers and brushes. The drying time for the side of the head treated with the compositions of the invention was 3.0±0.7 and 2.9±0.7 minutes for Examples 1 and 2, respectively. Example 2 left the dry hair slightly less tangled with significantly less flyaway and slight volume advantage. The drying time was significantly less than for untreated hair, which had a drying time of 3.3±0.7 for the control of Example 1 and 3.6±0.9 for the control of Example 2.

Example 3

An example of a 3-in-1 styling conditioner is set forth in the following Table

| Components | Amount |
| --- | --- |
| Demineralized water | q.s. 100% |
| Preservative | 1.5 |
| Polyquaternium-4 | 0.75 |
| Cetyltrimethylammonium bromide | 0.1 |
| Panthenol-DL | 0.5 |
| Glycerin | 2 |
| Wheat amino acids | 0.5 |
| Quaternium-80 | 0.2 |
| Polyvinylpyrrolidone | 0.75 |
| Phytantriol | 0.1 |
| PPG-5-Ceteth-20 | 0.75 |
| Silsurf C-208 (90% active) | 1 |

Example 4

An aerosol styling mousse is illustrated in the following Table

| Components | Amount |
| --- | --- |
| Demineralized water | q.s. 100% |
| Guar hydroxypropyltrimonium chloride | 0.09 |
| Preservative | .20 |
| Steareth-20 | 1.35 |
| Stearyl alcohol | 0.27 |
| Ceteareth-15 | 1.125 |
| Sodium methyl cocyl taurate (30% active in water diluent) | 0.99 |
| PVP/Dimethylaminoethylmethacrylate copolymer | 6.75 |
| Panthenol-DL | 0.225 |
| Wheat amino acids | 0.225 |
| Linoleamide DEA | 0.9 |
| Fragrance | 0.27 |
| Dimethyl paba amidolaurdimonium tosylate | 0.18 |
| Phytantriol | 0.045 |
| Citric acid | 0.02363 |
| Methyl gluceth 10 | 0.09 |
| Silsurf C-208 (90% active) | 1 |

The composition of the above Table is incorporated into a propellant-type system containing 92% of the composition of the Table and 8% isobutene/propane propellant.

Example 5

The following Table is an example of hair cream.

| Components | Amount |
| --- | --- |
| Demineralized water | q.s. 100% |
| Preservative | 0.4 |
| Ethylhexyl palmitate | 12 |

-continued

| Components | Amount |
| --- | --- |
| Benzophenone-3 (oxybenzone) | 0.1 |
| Alcohol SD 40B | 7 |
| Pearl protein | 0.001 |
| Fragrance | 0.05 |
| Sorbitan sesquioleate | 2 |
| Glycerin | 2 |
| Veegum | 0.2 |
| Guar hydroxypropyltrimonium chloride | 0.01 |
| Carbomer | 0.2 |
| PEG-40 Stearate | 2 |
| Sorbitan monostearate | 1 |
| Potassium hydroxide 45% | 0.05 |
| Dimethicone/cyclomethicone 15/85 | 0.5 |
| Benzyl alcohol | 0.5 |
| Silsurf C-208 (90% active) | 1 |

Example 6

A liquid hair lotion example is illustrated in the following Table

| Components | Amount |
| --- | --- |
| Demineralized water | q.s. 100% |
| Alcohol SD 40B | 35 |
| Propylene glycol | 10 |
| Glycerin | 15 |
| Fragrance | 0.1 |
| Wheat amino acids | 0.001 |
| Aloe/flower blend extract | 0.01 |
| Panthenol-DL | 0.001 |
| Phytantriol | 0.001 |
| Silsurf C-208 (90% active) | 1 |

Example 7

An example of a styling mousse is illustrated in the following Table

| Components | Amount |
| --- | --- |
| Demineralized water | q.s. 100% |
| PVP-60/VA (50% active in ethanol diluent) | 10 |
| Panthenol-DL | 0.5 |
| Disodium cocoamphocarboxypropionate | 0.7 |
| Fragrance | 2 |
| Polyethylene glycol 300-NF | 0.25 |
| Fragrance | 0.1 |
| 2-Phenoxyethanol | 1 |
| Citric acid | 0.01 |
| Alcohol SD 40B | 6 |
| Silsurf C-208 (90% active) | 1 |

Example 8

A styling shape gloss example is shown in the following Table

| Components | Amount |
| --- | --- |
| Demineralized water | q.s. 100% |
| Hydroxyethcellulose | 1 |
| Propylene glycol | 1 |
| Preservative | 0.2 |

-continued

| Components | Amount |
| --- | --- |
| Potassium hydroxide 45% | 0.01 |
| PVP/VA 70/30 copolymer (50% active) | 7 |
| Polysorbate-20 | 1 |
| Fragrance | 0.1 |
| Amodimethicone/laureth-6/PG blend | 1 |
| Methyldibromo glutamine | 0.2 |
| Silsurf C-208 (90% active) | 1 |

Example 9

A styling gel is illustrated in the following Table

| Components | Amount |
| --- | --- |
| Demineralized water | q.s. 100% |
| Carbopol | 0.9 |
| Phosphoric acid | 0.05 |
| Preservative | 0.2 |
| Alcohol SD 40B | 3.35 |
| PVP-60/VA (50% active) | 5 |
| Aminomethyl propanol (95% active) | 0.85 |
| Panthenol-DL | 0.25 |
| Wheat amino acids | 0.25 |
| Fragrance | 0.5 |
| Dimethyl paba amidolaurdimonium tosylate | 0.3 |
| Phytantriol | 0.05 |
| PPG-5-Ceteth-20 | 2 |
| Silsurf C-208 (90% active) | 1 |

Example 10

A styling putty is illustrated in the following Table

| Components | Amount |
| --- | --- |
| Demineralized water | q.s. 100% |
| Butylene glycol | 5 |
| Guar hydroxypropyl trimonium chloride | 1 |
| Citric acid | 0.1 |
| Disodium EDTA | 0.2 |
| PPG-5-Ceteth-20 | 2.5 |
| Steareth-21 | 2 |
| Cetearyl alcohol/ceteareth-20 | 4.5 |
| Glyceryl monostearate | 2.5 |
| PEG/PPG-8/3 laurate | 1 |
| Algae extract | 0.001 |
| Creatine | 0.001 |
| PVP/DMAPA acrylates copolymer | 6 |
| PEG-150 Pentaerythritol tetrastearate/C8-10 GLY | 4 |
| Preservative | 0.4 |
| Fragrance | 0.2 |
| Silsurf C-208 (90% active) | 1 |

Example 11

A texturing spray wax is illustrated in the following Table

| Components | Amount |
| --- | --- |
| Demineralized water | q.s. 100% |
| Propylene glycol | 3.5 |
| Sodium polystyrene sulfonate | 4 |
| Hydrolyzed wheat protein/wheat oligosaccharides-blend | 0.2 |

-continued

| Components | Amount |
| --- | --- |
| Creatine | 0.1 |
| Phenoxyethanol | 0.5 |
| Algae extract | 0.001 |
| PVP/VA copolymer (50% active). | 6 |
| Polyquaternium-11 | 0.25 |
| PPG 26 Buteth 26/PEG 40 hydrogenated castor oil | 0.25 |
| Silsurf C-208 (90% active) | 1 |

Example 12

A deep nourishing hair treatment is illustrated in the following Table

| Components | Amount |
| --- | --- |
| Demineralized water | q.s. 100% |
| Panthenol-DL | 0.01 |
| Creatine | 0.4 |
| Stearamidopropyl Dimethylamine | 1 |
| Behenyl TMAC/cetyl-stearyl alcohol | 4 |
| Benzophenone-3 (Oxybenzone) | 0.05 |
| Phytantriol | 0.001 |
| Amodimethicone | 0.5 |
| Dimethicone/dimethiconol 87/13% | 0.5 |
| Preservative | 1.0 |
| Dicetyldimonium chloride | 0.25 |
| Stearyl alcohol | 4 |
| Cetyl alcohol | 2 |
| Quaternium 18 | 0.25 |
| Glutamic acid | 0.2 |
| Glycolic acid (70%) | 0.2 |
| Sodium hydroxide solution 50% | q.s. desired pH |
| Wheat amino acids | 0.01 |
| Brazil nut oil/sunflower seed oil | 0.5 |
| Hibiscus sabdariffa flower extract | 0.1 |
| Guava extract | 0.1 |
| Corn kernel | 0.001 |
| Fragrance | 1.5 |
| Silsurf C-208 (90% active) | 1.0 |
| Color/dyes | 0.3 |

Example 13

A hair gel is illustrated in the following Table

| Components | Amount |
| --- | --- |
| Demineralized water | q.s. 100% |
| Hydroxycellulose | 2.25 |
| Preservative | 0.3 |
| POE (75M) lanolin | 0.1 |
| Linoleamidoproyl EDES/DLIS 85/15 | 3 |
| Sodium PCA 50% | 0.1 |
| Glycerin | 2.2 |
| Keratin amino acids | 0.1 |
| Panthenol-DL | 0.2 |
| Imidazolidinyl urea | 0.2 |
| Protein-hydrolized wheat | 0.5 |
| Polyvinylpyrrolidone | 1.5 |
| POE (20M) Sorbitan monolaurate | 1 |
| Dye | 0.1 |
| Propylene glycol | 3 |
| Phosphoric acid | 0 |
| Silsurf C-208 (90% active) | 1.0 |

Example 14

A hair conditioner is illustrated in the following Table

| Components | Amount |
| --- | --- |
| Demineralized water | Qs. 100 |
| Stearalkonium chloride 25% | 4 |
| Cetyl alcohol | 4 |
| Mineral oil | 2 |
| Steareth-2 | 0.75 |
| Allantoin | 0.1 |
| Algae extract | 0.5 |
| Dye | 0.1 |
| Glycerin | 1 |
| Propylene glycol | 0.964 |
| Glyceryl stearate/PEG-100 stearate | 0.75 |
| Benzoic acid | 0.2 |
| Preservative | 0.1 |
| Silsurf C-208 (90% active) | 1.0 |
| Triethanolamine 99% | 0.07 |

Example 15

A silk hair treatment is illustrated in the following Table

| Components | Amount |
| --- | --- |
| Demineralized water | Qs. 100 |
| Preservative | 0.5 |
| Hydroxyethyl cellulose | 0.5 |
| Stearalkonium chloride 25% | 4 |
| Isopropyl lanolate | 2 |
| Cetyl alcohol | 1.1 |
| Mineral oil | 1 |
| Isopropyl myristate | 0.5 |
| Stearic acid | 3.3 |
| Steareth-2 | 1 |
| PEG-40 stearate | 0.5 |
| Sodium PCA 50% | 0.1 |
| Sodium lactate 60% | 0.2 |
| Allantoin | 0.2 |
| Collagen amino acid | 0.42 |
| Hydrolyzed silk | 0.4 |
| Imidazolidinyl urea | 0.5 |
| Silk powder | 0.02 |
| Glycerin | 0.5 |
| Triethanolamine 99% | 0.36 |
| Fragrance | 0.2 |
| Silsurf C-208 (90% active) | 1.0 |

Example 16 a) The composition of Example 3 wherein Zonyl FSN-100 is incorporated at a 1% level in lieu of Silsurf C-208.

b) The composition of Example 5 wherein perfluorodecalin is incorporated at a 1% level in lieu of Silsurf C-208.

c) The composition of Example 9 wherein perfluorononyl dimethicone is incorporated at a 1% level in lieu of Silsurf C-208.

d) The composition of Example 12 wherein Surfynol 104 is incorporated at a 1% level in lieu of Silsurf C-208.

e) The composition of Example 13 wherein Q2-5211 Super-wetting Agent is incorporated at a 1% level in lieu of Silsurf C-208.

f) The composition of Example 14 wherein Zonyl FSK is incorporated at a 1% level in lieu of Silsurf C-208.

g) The composition of Example 15 wherein Fomblin HC/H-50 is incorporated at a 1% level in lieu of Silsurf C-208.

Various modifications of the compositions and method of the invention may be made without departing from the spirit or scope thereof and it is to be understood that the invention is intended to be limited only as defined in the appended claims.

What we claim is:

1. A method of styling wet hair comprising (A) applying to the wet hair of a person an aqueous leave-in composition that imparts hydrophobicity to the hair to cause dewetting of the hair comprising (a) a silicone polyether surfactant wetting agent consisting of a silicone polyether having a molecular weight from about 600 to about 2500 that causes dewetting and sheeting of water off hair without binding the silicone polyether surfactant wetting agent to hair, said silicone polyether surfactant wetting agent having a surface tension of from about 15 to 26 mN/m and exhibiting a Draves value of 100 seconds or less, (b) at least one hair treatment agent, and (c) a solvent system comprising water; (B) styling the hair while hydrated, and (C) during and/or after styling, allowing the hair to dry.

2. The method of claim 1 wherein the composition contains about 0.05 to 5% by weight of the wetting agent, and about 10 to 99% by weight of water.

3. The method of claim 1 wherein the hair is mechanically processed.

4. The method of claim 3 wherein the hair is blow dried.

5. The method of claim 4 wherein the composition is applied to damp hair.

6. The method of claim 1 wherein the wetting agent is a silicone polyether surfactant of the formula

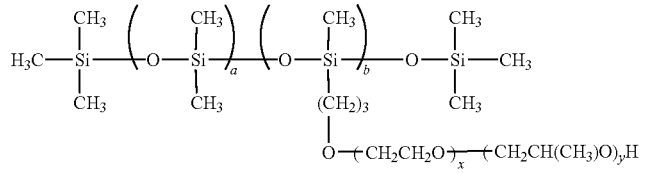

wherein a is an integer from 0 to 6; b is an integer from 2 to 4; x is an integer from 6 to 12, and y is an integer from 0 to 3.

7. The method of claim 6 wherein the wetting agent is a silicone polyether surfactant of the formula

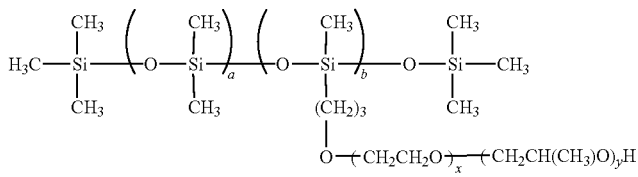

wherein a is an integer of from 1 to 3; b is an integer of from 2 to 4; x is 8, and y is 0.

8. The method of claim 1 wherein the composition contains 0.1 to 5% by weight of wetting agent, 0.1 to 5% by weight of hair treatment component, 35 to 95% by weight of water, and 0 to 40% by weight of alcohol, and wherein the wetting agent exhibits a Draves wetting value of about 30 seconds or less.

9. The method of claim 8 wherein the hair treatment component is a hair fixative polymer selected from the group consisting of anionic, nonionic, cationic, amphoteric, zwitterionic polymers, and combinations thereof.

10. The method of claim 8 wherein the hair treatment component is a cationic surfactant of the formula

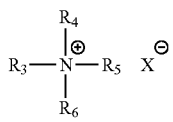

wherein (i) $R_3$ is a saturated or unsaturated hydrocarbon of 8 to 22 carbon atoms; (ii) $R_7CONJ\text{-}(CH_2)_n$ wherein $R_7$ is a saturated or unsaturated hydrocarbon of 7 to 21 carbon atoms and n is an integer of 1 to 4, or (iii) has the structure $R_8COO(CH_2)_n$ wherein $R_8$ is a saturated or unsaturated hydrocarbon of 7 to 21 carbons, and n is an integer of 1 to 4; $R_4$ has the definition of $R_3$ or hydrogen; $R_5$ and $R_6$ are individually hydrogen or an alkyl of 1 to 4 carbon atoms, and $X^-$ is an anion.

11. A method of decreasing the time to dry wet hair comprising (A) applying to the wet hair of a person an aqueous leave-in hair styling composition that imparts hydrophobicity to the hair to cause dewetting of the hair comprising (a) at least one silicone polyether surfactant wetting agent consisting of a silicone polyether having a molecular weight from about 600 to about 2500 that causes dewetting and sheeting of water off hair without binding the silicone polyether surfactant wetting agent to hair, said silicone polyether surfactant wetting agent having a surface tension from about 15 to 26 mN/m and exhibiting a Draves wetting value of 100 seconds or less; (b) at least one hair treatment agent, and (c) a solvent system comprising water, and (B) drying the hair.

12. The method of claim 11 wherein the composition contains about 0.1 to 5% by weight of wetting agent, and about 10 to 99% by weight of water.

13. The method of claim 11 wherein the composition contains about 0.1 to 5% by weight of wetting agent, about 35 to 95% by weight of water, and optionally comprising 0 to about 40% by weight of a low molecular weight alcohol, the wetting agent exhibiting a Draves wetting value of about 30 seconds or less.

14. The method of claim 11 wherein the hair is blow dried.

15. The method of claim 11 wherein the hair is towel dried.

16. The method of claim 11 wherein the composition contains about 1 to 5% by weight hair treatment agent.

17. The method of claim 11 wherein the hair treatment component is a hair fixative polymer selected from the group consisting of anionic, nonionic, cationic, amphoteric, zwitterionic polymers, and combinations thereof.

18. The method of claim 11 wherein the hair treatment component is a cationic surfactant of the formula

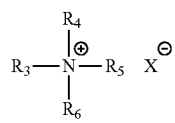

wherein (i) $R_3$ is a saturated or unsaturated hydrocarbon of 8 to 22 carbon atoms; (ii) $R_7CONJ\text{-}(CH_2)_n$ wherein $R_7$ is a saturated or unsaturated hydrocarbon of 7 to 21 carbon atoms and n is an integer of 1 to 4, or (iii) has the structure $R_8COO(CH_2)_n$ wherein $R_8$ is a saturated or unsaturated hydrocarbon of 7 to 21 carbons, and n is an integer of 1 to 4; $R_4$ has the definition of $R_3$ or hydrogen; $R_5$ and $R_6$ are individually hydrogen or an alkyl of 1 to 4 carbon atoms, and $X^-$ is an anion.

19. The method of claim 11 wherein the wetting agent is a silicone polyether surfactant of the formula

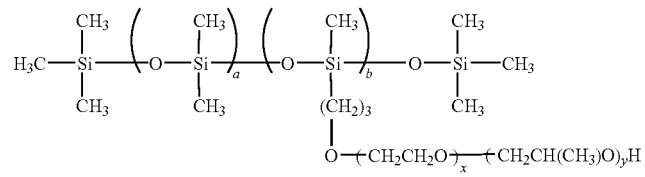

wherein a is an integer from 0 to 6; b is an integer from 2 to 4; x is an integer from 6 to 12, and y is an integer from 0 to 3.

20. The method of claim 11 wherein the wetting agent is a silicone polyether surfactant of the formula

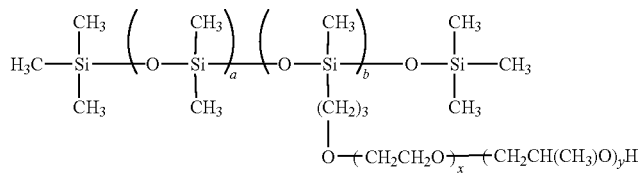

wherein a is an integer of from 1 to 3; b is an integer of from 2 to 4; x is 8, and y is.

21. The method of claim 13 wherein the composition contains about 0.1 to 5% by weight of hair treatment component, about 1 to 40% by weight of alcohol, and about 0.001 to 10% by weight of volatile solvent other than the alcohol.

22. A method of styling wet hair comprising (A) applying to damp hair of a person an aqueous leave-in composition that imparts hydrophobicity to the hair to cause dewetting of the hair comprising (a) a silicone polyether surfactant wetting agent consisting of a silicone polyether having a molecular weight from about 600 to about 2500 that causes dewetting and sheeting of water off hair without binding the silicone polyether surfactant wetting agent to hair, said silicone polyether surfactant wetting agent having a surface tension of from about 15 to 26 mN/m and exhibiting a Draves value of 100 seconds or less, (b) at least one hair treatment agent, and (c) a solvent system comprising water; (B) styling the hair while hydrated, and (C) during and/or after styling, allowing the hair to dry.

23. A method of decreasing the time to dry wet hair comprising (A) applying to damp hair of a person an aqueous leave-in hair styling composition that imparts hydrophobicity to the hair to cause dewetting of the hair comprising (a) at least one silicone polyether surfactant wetting agent consisting of a silicone polyether having a molecular weight from about 600 to about 2500 that causes dewetting and sheeting of water off hair without binding the silicone polyether surfactant wetting agent to hair, said silicone polyether surfactant wetting agent having a surface tension from about 15 to 26 mN/m and exhibiting a Draves wetting value of 100 seconds or less, (b) at least one hair treatment agent, and (c) a solvent system comprising water, and (B) drying the hair.

\* \* \* \* \*